US012595446B2

(12) United States Patent
     Hu

(10) Patent No.:     US 12,595,446 B2
(45) Date of Patent:          Apr. 7, 2026

(54) INCUBATOR

(71) Applicant: SHANGHAI WOLWO STEM CELL TECHNOLOGY CO., LTD., Shanghai (CN)

(72) Inventor: Gengxi Hu, Shanghai (CN)

(73) Assignee: SHANGHAI WOLWO STEM CELL TECHNOLOGY CO., LTD., Shanghai (CN)

( * ) Notice: Subject to any disclaimer, the term of this patent is extended or adjusted under 35 U.S.C. 154(b) by 615 days.

(21) Appl. No.: 18/005,558

(22) PCT Filed: Jul. 15, 2021

(86) PCT No.: PCT/CN2021/106395
     § 371 (c)(1),
     (2) Date: Jan. 13, 2023

(87) PCT Pub. No.: WO2022/012607
     PCT Pub. Date: Jan. 20, 2022

(65)                Prior Publication Data
     US 2023/0265370 A1      Aug. 24, 2023

(30)          Foreign Application Priority Data
     Jul. 17, 2020    (CN) .......................... 202021416351.8

(51) Int. Cl.
     *C12M 1/00*           (2006.01)
     *C12M 1/02*           (2006.01)
                    (Continued)
(52) U.S. Cl.
     CPC .............. *C12M 1/12* (2013.01); *C12M 1/005* (2013.01); *C12M 1/02* (2013.01); *C12M 1/38* (2013.01);
                    (Continued)

(58) Field of Classification Search
     CPC .............................. C12M 1/005; C12M 41/14
     See application file for complete search history.

(56)                References Cited

U.S. PATENT DOCUMENTS

2003/0092178 A1    5/2003  Yerden
2005/0105172 A1*   5/2005  Hasegawa .............. C12M 23/50
                                                    359/368
                    (Continued)

FOREIGN PATENT DOCUMENTS

CN        102978112 A      3/2013
CN        107012088 A      8/2017
                    (Continued)

OTHER PUBLICATIONS

First Office Action issued for Chinese Patent Application No. 202180045181.8, dated Jan. 27, 2024, 11 pages including English machine translation.
                    (Continued)

*Primary Examiner* — Jonathan M Hurst
(74) *Attorney, Agent, or Firm* — HSML P.C.

(57)                ABSTRACT

Provided in the present invention is an incubator capable of producing pressure fluctuations. The incubator comprises an incubator body and a variable pressure apparatus, the incubator body having a variable pressure interface, the variable pressure apparatus being connected to the incubator body by means of the variable pressure interface, and the variable pressure apparatus being used for inputting fluctuating or constant air pressure into the incubator body.

16 Claims, 4 Drawing Sheets

(51) Int. Cl.

| | |
|---|---|
| *C12M 1/107* | (2006.01) |
| *C12M 1/12* | (2006.01) |
| *C12M 1/38* | (2006.01) |

(52) U.S. Cl.

CPC ............ *C12M 23/36* (2013.01); *C12M 29/00* (2013.01); *C12M 41/14* (2013.01)

(56) References Cited

U.S. PATENT DOCUMENTS

| | | | |
|---|---|---|---|
| 2008/0199944 A1* | 8/2008 | Lee ........................ | C12M 41/14 |
| | | | 435/286.6 |
| 2009/0111180 A1 | 4/2009 | Vilendrer et al. | |
| 2017/0002306 A1* | 1/2017 | Cecchi ................... | C12M 41/34 |

FOREIGN PATENT DOCUMENTS

| | | |
|---|---|---|
| CN | 206721213 U | 12/2017 |
| CN | 207793283 U | 8/2018 |
| CN | 109370905 A | 2/2019 |
| CN | 209243075 U | 8/2019 |
| CN | 209685811 U | 11/2019 |
| CN | 209989413 U | 1/2020 |
| CN | 212025366 U | 11/2020 |
| JP | 2004242581 A | 9/2004 |
| WO | 2015138999 A1 | 9/2015 |
| WO | 20190129799 A1 | 7/2019 |

OTHER PUBLICATIONS

Search Report issued for Chinese Patent Application No. 202180045181. 8, dated Jan. 23, 2024, 2 pages.

International Search Report issued for International Patent Application No. PCT/CN2021/106395, Date of mailing: Oct. 11, 2021, 5 pages including English translation.

Office Action issued for Chinese Patent Application No. 202021416351. 8, dated Feb. 19, 2021, 4 pages including partial English machine translation.

Supplementary European Search Report and Written Opinion issued for European Patent Application No. 21842971.0, dated Nov. 10, 2025, 6 pages.

\* cited by examiner

INCUBATOR

TECHNICAL FIELD

The present invention relates to an incubator.

BACKGROUND ART

An incubator is a box-like apparatus mainly used for culturing the cells of microorganisms, plants and animals. It provides stable temperature, humidity and gas concentration by simulating the growing environment of microorganisms, tissues, cells, etc. The incubator has been widely used for culturing cells and tissues and for breeding and culturing some special microorganisms. A three-gas incubator, working on the same principle as other incubators, is featured with that besides $CO_2$, nitrogen and oxygen can also be added therein, and the content of a variety of different gases can be controlled and adjusted.

The pressure in most of the incubators is not higher than the atmospheric pressure and is largely set to a constant pressure. An invention patent application with the Publication Number "CN102978112A" discloses a high-pressure cell incubator, which maintains, in a high-pressure environment, a constant pressure required for cell culture within an incubator body and avoids excessive gas pressure occurring within the incubator body due to the fact that a gas flows therein too fast by using an ordinary valve. A first valve and a second valve are both needle valves, and a gas, within the incubator body, passing through the first valve and the atmosphere passing through the second valve sequentially go through an oxygen pressure reducer and a flow meter and then enter a gas analyzer, thereby controlling the quantity of the sampled gas. However, the inventor found that a good culture effect could be achieved by applying an additional constant pressure into the incubator, in particular the three-gas incubator, and furthermore, a better culture effect could be achieved by allowing an environment for culturing stein cells to be closer to that in a human body when pressure applied into the incubator changes sinusoidally over time.

SUMMARY OF THE INVENTION

An object of the present invention is to provide an incubator capable of producing pressure fluctuations.

According to an embodiment of the present invention, an incubator comprises an incubator body, wherein the incubator further comprises a variable pressure apparatus, the incubator body has a variable pressure interface, the variable pressure apparatus is connected to the incubator body, via the variable pressure interface, and the variable pressure apparatus is configured to input fluctuating or constant gas pressure into the incubator body.

According to an embodiment of the present invention, the variable pressure apparatus comprises a cylinder body and a piston, the cylinder body is communicated to the incubator body via the variable pressure interface, and the piston is movably disposed in the cylinder body so as to input the gas pressure by means of the movement of the piston.

According to an embodiment of the present invention, the cylinder body is connected to the variable pressure interface directly or via a pipe.

According to an embodiment of the present invention, the cylinder body is directly connected to the variable pressure interface, and the variable pressure interface is large enough to allow the cylinder body and the incubator body to synchronously change in gas pressure along with the movement of the piston.

According to an embodiment of the present invention, the cylinder body is fixedly connected to the incubator body, and preferably, the cylinder body is fixedly connected to the top of the incubator body.

According to an embodiment of the present invention, the variable pressure apparatus further comprises one of an electric cylinder, a pneumatic cylinder, and a hydraulic cylinder; preferably, the electric cylinder comprises a servo motor and a transmission mechanism, and the transmission mechanism connects the servo motor and the piston to convert the rotation of the servo motor into the movement of the piston; and preferably, the electric cylinder is an electric push rod, which can drive the piston to move.

According to an embodiment of the present invention, the variable pressure apparatus comprises a gas storage tank, which is communicated to the incubator body via a pressurization gas circuit and a decompression gas circuit;

the pressurization gas circuit is provided with a pressurization pump and a pressurization control valve, the pressurization pump is configured to transport a gas in the gas storage tank to the incubator body, and the pressurization control valve is configured to control the on-off of the pressurization gas circuit; and the decompression gas circuit is provided with a decompression pump and a decompression control valve, the decompression pump is configured to transport a gas in the incubator body to the gas storage tank, and the decompression control valve is configured to control the on-off of the decompression gas circuit.

According to an embodiment of the present invention, the incubator body is further provided with a safety valve, which is opened after the pressure in the incubator body exceeds a safety threshold.

According to an embodiment of the present invention, the incubator body further comprises an operable/closable gas inlet and an operable/closable gas outlet, independent of the variable pressure interface.

According to an embodiment of the present invention, a sterilization apparatus or/and a humidification apparatus or/and an electric heating apparatus is/are disposed in the incubator body.

According to an embodiment of the present invention, the sterilization apparatus is an ultraviolet light emitter or a steam sterilization apparatus.

According to an embodiment of the present invention, one or more types of gases are present in the incubator, preferably a three-gas incubator; and more preferably, the gases comprise carbon dioxide, nitrogen, and oxygen.

According to an embodiment of the present invention, the incubator further comprises a gas replenishing system, in which a gas relief apparatus is configured to release the gas within the incubator body; and a gas supply system is configured to supply a gas with stable process parameters to the incubator body while the pressure relief apparatus performs releasing.

According to an embodiment of the present invention, a gas mixing apparatus is disposed within the incubator body and is configured to keep the gas in the incubator body in a turbulent state so as to maintain the uniformity of the gas.

According to an embodiment of the present invention, the gas supply system comprises a premixing tank, which receives the one or more types of gases via an input pipeline and is connected to the incubator body via an output pipeline, a gas mixing apparatus is disposed within the premixing tank, the input pipeline is provided with a gas source control apparatus for a gas source, and the output pipeline is provided with an incoming gas control apparatus for the incubator body.

According to an embodiment of the present invention, a gas control apparatus is further disposed within the premixing tank, and the gas control apparatus comprises a gas concentration detecting meter, a heating apparatus, a humidification apparatus and/or a temperature/humidity detection apparatus.

According to an embodiment of the present invention, the gas source control apparatus and/or the incoming gas control apparatus comprises a heating apparatus, a humidification apparatus or/and a gas filter apparatus.

According to the foregoing solution, due to the capability of providing additionally applied pressure fluctuations, the incubator can be used to simulate a pressure environment where cells exist, thereby helping to improve the biological activity of the cells. In addition, a good culture effect is also achieved by the provision of a constant pressure environment.

BRIEF DESCRIPTION OF THE DRAWINGS

The above and other features, properties and advantages of the present invention will become more obvious from the following description combined with the accompanying drawings and embodiments, in which.

DETAILED DESCRIPTION OF THE INVENTION

Figure 1:
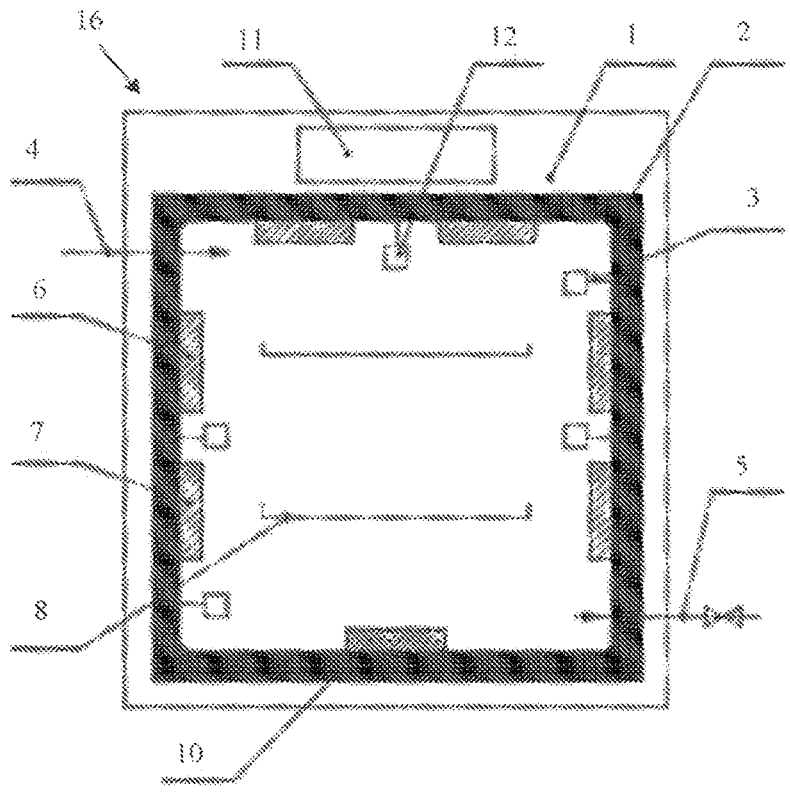
FIG. 1 illustrates a sectional view of an incubator body of an incubator.
Figure 2:
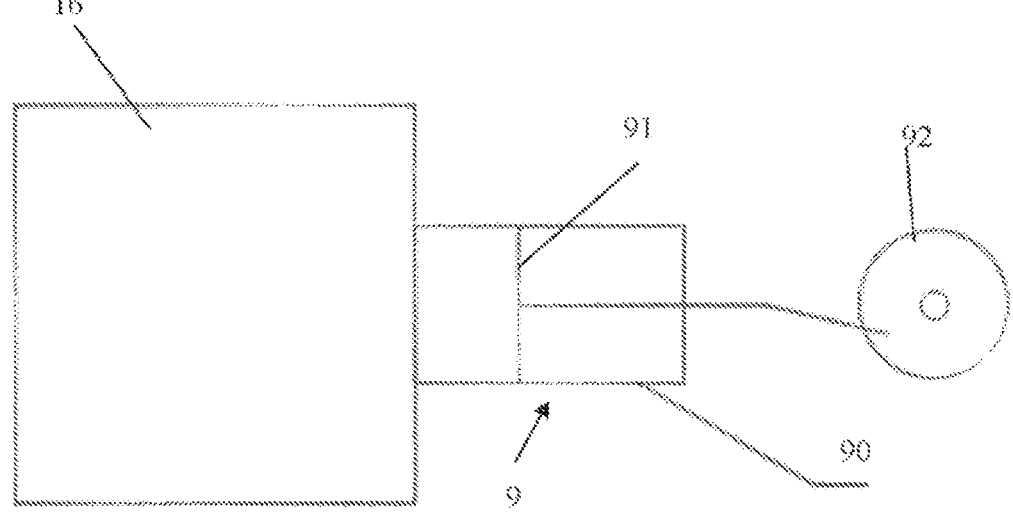
FIG. 2 illustrates a schematic diagram of an incubator in a first embodiment.
Figure 3:
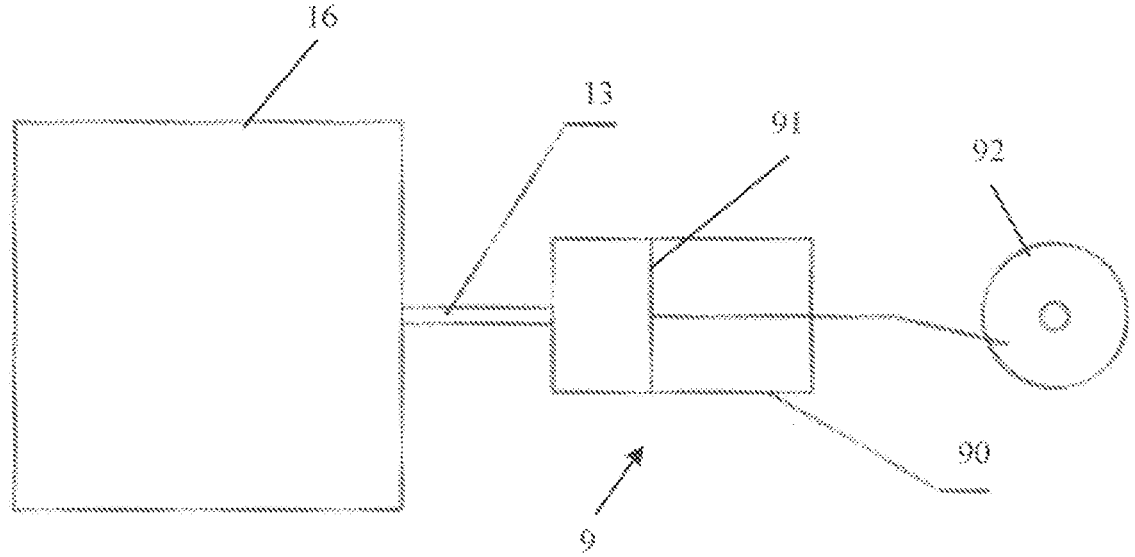
FIG. 3 illustrates a schematic diagram of an incubator in a second embodiment.

As illustrated in FIGS. 1 and 2, the incubator comprises an incubator body 16 and a variable pressure apparatus 9. The incubator body 16, with a configuration similar to that of an existing incubator, provides a space and environment for culturing cells. The following embodiments will be explained by taking a three-gas incubator as an example, but not limited thereto. As illustrated in FIG. 1, the incubator body 16 comprises a chamber 3, and further comprises a gas inlet 4 at the upper part thereof and a gas outlet 5 at the bottom thereof, and the chamber 3 is internally provided with a holder 8 for holding tools such as a microbial culture dish. As illustrated in FIG. 2, the variable pressure apparatus 9 comprises a cylinder body 90 and a piston 91. The cylinder body 90 is externally connected to the incubator body 16. The incubator body 16 has a variable pressure interface that is not illustrated in the figure. By means of the variable pressure interface, a space inside the cylinder body 90 is communicated to the chamber 3, such that a gas within the cylinder body 90 may be compressed by moving the piston 91, thereby, inputting gas pressure to the chamber 3. Inputting the gas pressure may be inputting positive or negative pressure. As illustrated in FIG. 2, when the piston 91 moves to the left, a positive pressure is input, and when it moves to the right, negative pressure is input. The size of variable pressure interface may be configured to be almost the same as the cross section of the cylinder body 90, such that the space in the cylinder body 90 and a space in the chamber 3 are almost the same one, and with the movement of the piston 91, an internal gas pressure may change synchronously. In another embodiment, the variable pressure interface is configured smaller, there is a delay in the gas pressure change between the cylinder body 90 and the chamber 3, and the gas pressures inside the two become equal only after the piston 91 stops moving for a while. FIG. 3 illustrates another embodiment, which differs from the embodiments illustrated in FIGS. 1 and 2 in that the variable pressure interface is connected to the variable pressure apparatus 9 via a pipe 13. In this way, the variable pressure apparatus 9 and the incubator body 16 may be arranged at a distance, and the spatial arrangement of the variable pressure apparatus 9 and the incubator body 16 is more flexible. Instead of being combined into a whole, the variable pressure apparatus 9 and the incubator body 16 may be separately manufactured by different industrial divisions, which can save costs or facilitate the productization of the apparatus. In the foregoing embodiment, the movement of the piston 91 is implemented by connecting of a drive apparatus 92, which is an electric cylinder comprising a servo motor and a transmission mechanism in one embodiment. The servo motor rotates at a changeable output speed, and the transmission mechanism converts the rotation of the servo motor into the movement of the piston 91. The transmission mechanism is, for example, a rack-and-pinion or screw-and-nut transmission mechanism. In a preferred embodiment, the drive apparatus 92 is an electric push rod. In another embodiment, the drive apparatus 92 is a pneumatic cylinder or a hydraulic cylinder. By means of the reciprocating motion of the piston 9:1, the gas in the incubator body 16 produces a fluctuating pressure, and the change of the pressure may be configured as required, for example, configured to be a sinusoidal change. When the piston 91 moves to a certain position and then remains stationary, a constant pressure may be produced in the incubator body. The incubator body 16 is provided with a safety valve that is not illustrated in the figure, and when the pressure exceeds a certain value, the safety valve is opened to release the pressure automatically. The safety valve is also suitable for the embodiments described below.

Figure 4:
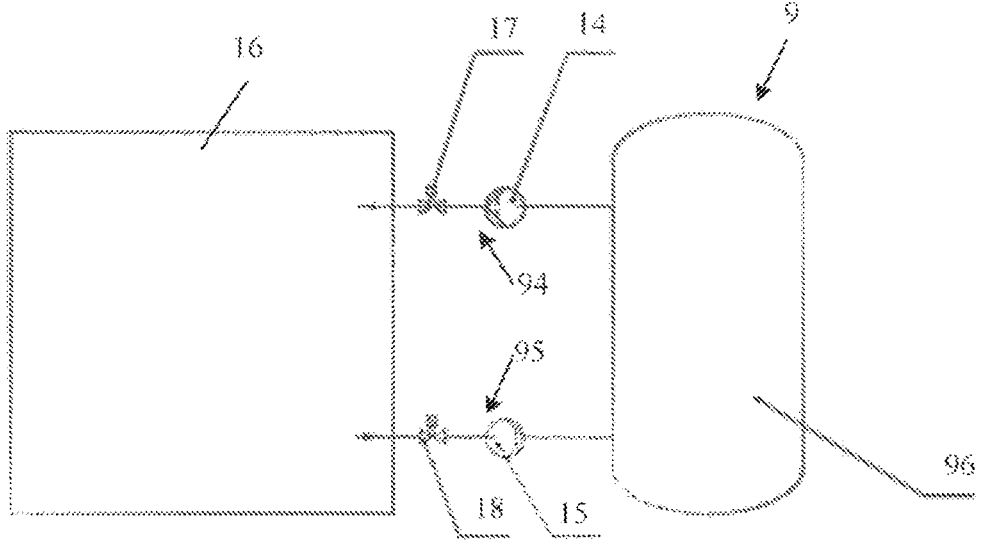
FIG. 4 illustrates a schematic diagram of an incubator in a third embodiment.

FIG. 4 illustrates a yet another embodiment, Compared with the embodiments illustrated in FIG. 1 and FIG. 2, the difference lies in that the variable pressure apparatus 9 comprises a gas storage tank 96, a pressurization gas circuit 94 and a decompression gas circuit 95. The gas storage tank 96 is connected to the incubator body 16 via the pressurization gas circuit 94 and the decompression gas circuit 95 respectively. The pressurization gas circuit 94 is provided with a pressurization pump 14 and a pressurization control valve 17. The pressurization pump 14 is configured to transport the gas in the gas storage tank 96 to the incubator body 16, and the pressurization control valve 14 is configured to control the on-off of the pressurization gas circuit.

The decompression gas circuit 95 is provided with a decompression pump 15 and a decompression control valve 18. The decompression pump 15 is configured to transport the gas in the incubator body 16 to the gas storage tank 96, and the decompression control valve 18 is configured to control the on-off of the decompression gas circuit.

When the pressure in the chamber 3 needs to be increased, the control valve 17 in front of the pressurization pump 14 is opened; the pressurization pump 14 starts to pump the gas from the gas storage tank 96 into the chamber 3; the control valve 18 in front of the decompression pump 15 is closed; and the pressure in the chamber 3 increases to a pressure value to end the pressurization. Then, the control valve 17 in front of the pressurizing pump 14 is closed; the control valve 18 in front of the decompression pump 15 is opened; the decompression pump 15 pumps the gas from the chamber 3 into the gas storage tank 96; and the pressure of the chamber 3 decreases to a specified value to end the decompression. The pressurization pump 14, the decompression pump 15, and the two control valves 17 and 18 may be connected to a controller, in which pressurization and decompression operations are controlled by means of a program, and the pressure in the chamber 3 fluctuates periodically over time.

More detailed configurations may also be implemented on the incubator body 16. As illustrated in FIG. 1, a housing 1 of the incubator body 16 of the incubator is a stainless steel tank, which may be a cylinder or a cuboid with circular arc transitions at inner walls. The stainless steel tank has a cover that is integrated with an incubator door, and may withstand a certain positive pressure after being closed. The bottom of the chamber 3 is provided with a humidification apparatus 10, and a sensor or a tester 12 is arranged around the humidification apparatus 10 and is connected to an externally disposed display that is not illustrated in the figure. The sterilization apparatus 6 may be an ultraviolet light emitter arranged around the chamber 3, or may provide steam sterilization. The heating apparatus 7 provides electric heating and is distributed around the chamber 3. A cell culture environment is purified by means of the sterilization apparatus 6; a more realistic culture environment is simulated by means of the heating apparatus and the humidification apparatus; furthermore, the sensor or tester 12 may be used to provide feedback information such as temperature, humidity, and pressure, and feed the feedback information to the controller, which then compares the feedback information with a set value to control and adjust the heating apparatus 7 and humidification apparatus 10, etc.

An embodiment of the application of an incubator is described below.

"Different conditions" or "different culture conditions" means that cell culture conditions involved in the comparison differ from each other only by the unique characteristics of a gas environment indicated below, and such a set of different culture conditions for comparison is referred to as "four conditions" for short:

normoxia (20%): the oxygen concentration is 20%, and no additional pressure is applied beyond one atmospheric pressure;

hypoxia (5%): the oxygen concentration is 5%, and no additional pressure is applied beyond one atmospheric pressure;

hypoxic static pressure (5%+ static): the oxygen concentration is an additional constant pressure of 95 mmHg is applied at one atmospheric pressure, the incubator body 16 is pressurized by means of the variable pressure apparatus 9, when the additionally applied pressure reaches 95 mmHg, the incoming and outgoing gases of the incubator body 16 are allowed to reach a dynamic balance without stopping inflation and pressurization, and the gas in the incubator body 16 is maintained at one atmospheric pressure+95 mmHg; and hypoxic dynamic pressure (5%+ dynamic): the oxygen concentration is 5%, an additional pressure is applied at one atmospheric pressure, and the pressure in the incubator body 16 periodically fluctuates sinusoidally in the range of 1 atmospheric pressure+(75-115) mmHg, with the frequency of 14 times/min.

Embodiment: Comparison of Expansion Folds of Hair Follicle Mesenchymal Stem Cells Cultured Under Different Conditions 1) To obtain intact human hair follicle tissues, the hair follicle tissues were carefully placed at the bottom of a 1.5 mL EP tube by using microforceps. 5 μL of enzymolysis solution TripLE (Gibco-12604021) was added to each hair follicle; the tube was then let stand in the incubator filled with 5% $CO_2$ at 37° C. for 3 hours; the bottom of the tube was carefully flicked every hour; and the resulting mixture was gently mixed.

2) After 3 hours of enzymolysis, it could be seen under a microscope that an outer root sheath of each hair follicle was completely enzymolyzed, but the hair shaft could not be completely enzymolyzed. Without removing the unenzymolyzed part, the enzymolysis solution was blown 10 times by using a 100-1000 μL pipette to completely mix the enzymolysis solution. The enzymolysis solution was let stand for 1 minute until the unenzymolyzed hair shaft sunk to the bottom of the EP tube, and the upper enzymolysis suspension, i.e., the primary mesenchymal stem cells, was sucked.

25 μL of enzymolytic primary mesenchymal stem cell suspension obtained by combining the enzymolysis solutions of 5 hair follicles was added to one well of a six-well plate, and then 2 mL of amniotic fluid medium (purchased from Guangzhou Baiyunshan Baidi Biotechnology Co., Ltd.) was added for resuspension. The six-well plate was cultured under the four conditions including normoxia (20%), hypoxia (5%), hypoxic static pressure (5%+ static), and hypoxic dynamic pressure (5%+ dynamic) at 37° C., and the medium was changed every 3 days.

3) After culturing for 10-12 days, the culture medium could be discarded when the cell density in the six-well plate reached more than 80%; 0.5 mL of TryplE digestion solution was added to the bottom of the six-well plate, which was then placed in a 37° C. incubator for 3-minute digestion; then, 1 mL of amniotic fluid medium was added to the six-well plate to terminate the digestion; the supernatant was removed and placed in a 15 mL centrifuge tube; the well plate was rinsed once with 1 mL of amniotic fluid medium; the rinse solution was added to the centrifuge tube. The centrifuge tube was centrifuged at 1500 rpm for 5 minutes in a centrifuge; the supernatant was discarded; 1 mL of amniotic fluid medium was added for resuspension; the cells were counted and inoculated into a T25 culture flask, and cultured to obtain P1-generation hair follicle mesenchymal stem cells.

4) The cells were continuously subcultured to the P12 generation, and the cells under the four conditions were always maintained under their respective culture conditions. Expansion fold=count of cells harvested per passage/count of inoculated cells. In this embodiment, the cells were passaged strictly according to the density of 5000 cells/cm². The area of a T25 culture flask was 25 cm², that is, a T25 culture flask was inoculated with $1.25 \times 10^5$ cells each time, and the calculation formula of the expansion fold is "expansion fold=count of cells per harvest/(1.25×10⁵)".

Figure 5:
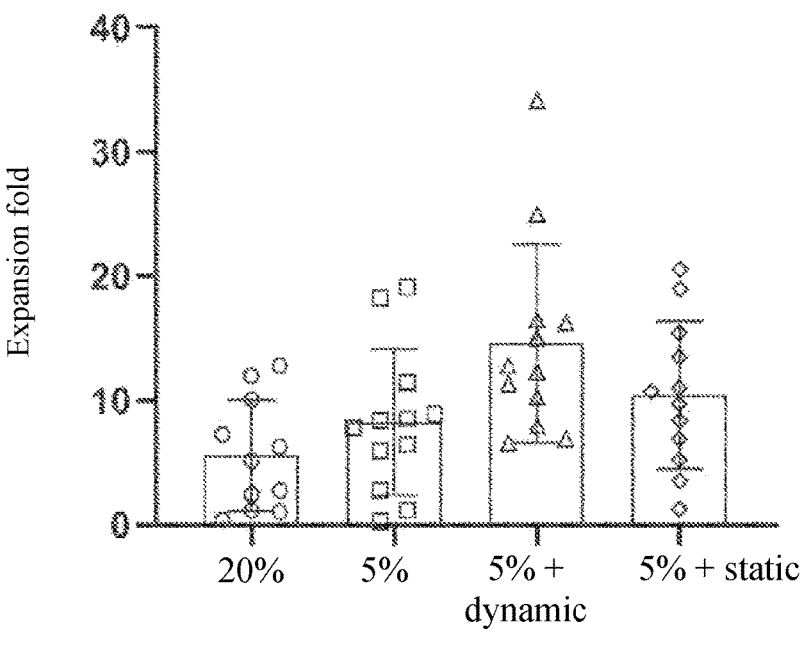
FIG. 5 illustrates expansion folds of hair follicle mesenchymal stem cells cultured under different conditions within an incubator in an application example.
Figure 6:
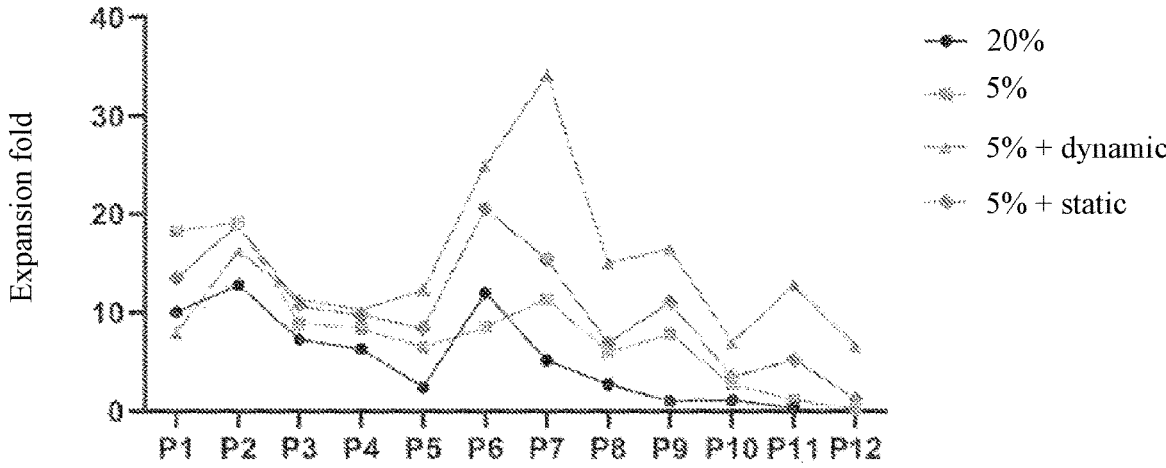
FIG. 6 illustrates passage numbers and expansion folds of hair follicle mesenchymal stem cells cultured under different conditions within an incubator in an application example, in which the passage number is represented by Pn, with n being a natural number.
Figure 7:
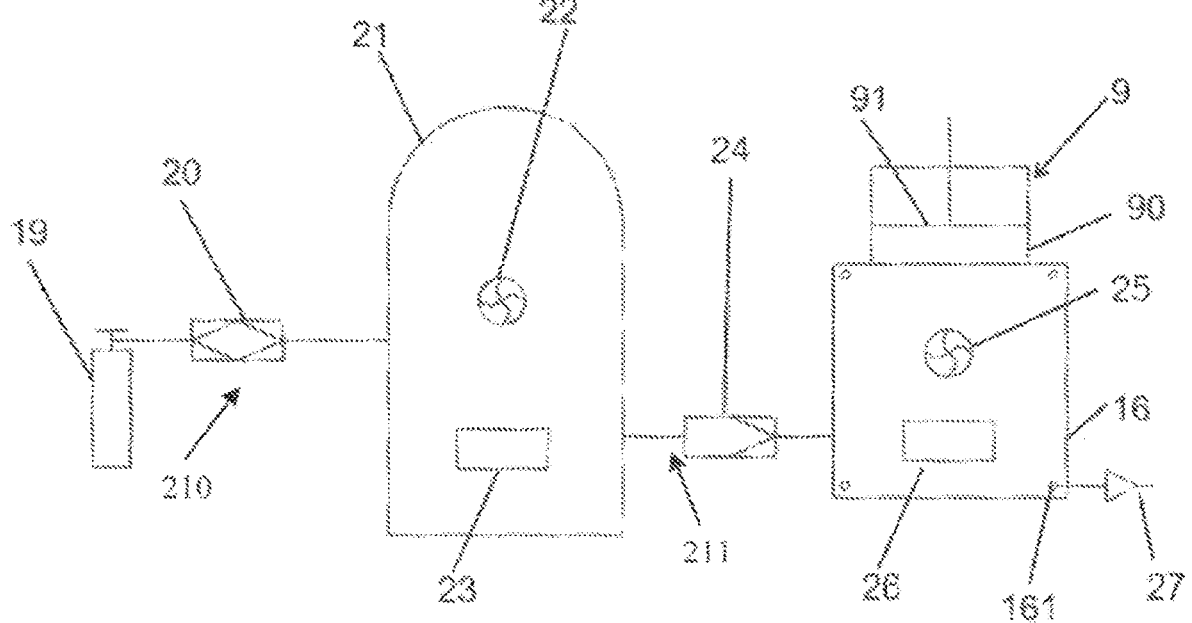
FIG. 7 is a schematic diagram of an incubator in a fourth embodiment.

The results were shown in FIG. 5 and FIG. 6. The results showed that the expansion fold of mesenchymal stem cells cultured in hypoxia was higher than that in normoxia, the expansion fold was further increased by pressurization, and the expansion fold of mesenchymal stem cells was the highest under the hypoxic dynamic pressure condition, FIG. 7 shows an incubator in still another embodiment. The incubator comprises an incubator body 16, a variable pressure apparatus 9 and a gas premixing tank 21. This embodiment follows the reference signs of elements and some of the content of the previous embodiment, in which like reference signs are used to represent the same or similar elements, and the explanation of the same technical content is selectively omitted. For the explanation of the omitted part, reference may be made to the foregoing embodiment, and the explanation will not be repeated in this embodiment. Compared with the embodiment illustrated in FIG. 2, FIG. 3 or FIG. 4, this embodiment is different in that a cylinder body 90 of the variable pressure apparatus 9 is fixedly connected to the top of the incubator body 16 by means of welding as one of fixed connection methods. In this way, the overall structure is more compact, firm, and reliable, and can withstand higher gas pressure and higher-frequency gas pressure fluctuations. A variable pressure interface that is not illustrated in the figure is between the incubator body 16 and the variable pressure apparatus 9. The space in the cylinder body 90 is communicated to the incubator body 16 via the variable pressure interface, such that the gas in the cylinder body 90 can be compressed by moving the piston 91, thereby inputting gas pressure to the incubator body 16. The input gas pressure may be a positive or negative pressure. When the piston 91 moves downwards, a positive pressure is input, and when it moves upwards, a negative pressure is input. The variable pressure interface may be configured to be almost the same size as the cross section of the cylinder body 90, such that the space in the cylinder body 90 and a space in the incubator body 16 are almost the same space, and with the movement of the piston 91, an internal gas pressure may change synchronously.

In various embodiments, the incubator may further optionally comprise a gas replenishing system, which can be used in any of the preceding embodiments. The gas replenishing system comprises a gas supply system and a pressure relief apparatus. The pressure relief apparatus is configured to release the gas in the incubator body. The gas supply system is configured to supply a gas with stable process parameters to the incubator body while the gas in the incubator body is released, to ensure the stability of the process parameters of the gas in the incubator body. The gas supply system is also configured to reduce the fluctuation of a gas atmosphere in the incubator body, to ensure a more stable culture environment. The process parameters comprise, but are not limited to, gas concentration, gas temperature, and gas humidity.

In the embodiment illustrated in FIG. 7, the gas supply system comprises a gas source 19, a gas premixing tank 21, a gas source control apparatus 20, and an incoming gas control apparatus 24. The function of the gas premixing tank 21 is to mix various gases and adjust the process parameters of the gas, and the gas source 19 provides the gas (for example, the mixed gas of oxygen, carbon dioxide and nitrogen) required for the culture environment. The gas source 19 provides one or more gases, such as nitrogen, carbon dioxide, oxygen, air, or other gases. The gas premixing tank 21 has an input pipeline 210 and an output pipeline 211, a gas source control apparatus 20 is disposed in the input pipeline 210, and an incoming gas control apparatus is disposed in the output pipeline 211. The gas source control apparatus 20 comprises various valves, for example, one or more of a pressure regulating valve and a control valve. The gas source control apparatus further comprises one or more of a heating apparatus, a humidification apparatus, and a filter apparatus. The control valve is configured to control the on-off of the pipeline, the pressure regulating valve is configured to control the output pressure of the pipeline, and the control valve is preferably a one-way valve. The heating apparatus is configured to preheat the gas passing through the pipeline, and the heating apparatus may be selected from a jacket heater, a coil heater, or an electric heater. The humidification apparatus is configured to add water vapor to increase the humidity of the gas within the pipeline. A method for adding the water vapor may be selected from spraying or injecting the water vapor into the pipeline. The incoming gas control apparatus 24 comprises, but is not limited to, one or more of a pressure regulating valve and a control valve which is preferably a one-way valve. The incoming gas control apparatus 24 may further optionally comprise a heating apparatus, a humidification apparatus, or a gas filter apparatus, and the gas filter apparatus is preferably a high-efficiency gas filter apparatus with a pore size not greater than 0.3 μm. A gas mixing apparatus 22 and a gas control apparatus 23 are disposed in the premixing tank 21. The mixing apparatus 22 is activated when the gas source 19 provides various gases, and a fan or an air pump may be selected to produce a turbulent flow in the premixing tank 21. The gas control apparatus 23 comprises, but is not limited to, various gas concentration detecting meters, heating apparatuses, humidification apparatuses, temperature/humidity detection apparatuses, etc.

The gas comes out from the gas source 19 and enters the premixing tank 21 after being adjusted by the gas source control apparatus 20. The gas passes through the gas mixing apparatus 22 to allow the gas in the premixing tank 21 to be mixed evenly. After the gas is adjusted to a set value by the gas control apparatus 23 in the premixing tank 21, the gas may be introduced into the incubator 16 by means of the incoming gas control apparatus 24. According to the flow direction of the gas in the incubator body 16, one or more gas outlet holes 161 are arranged in parts that are difficult to reach by the gas flow; automatic gas releasing is effected by means of the gas relief apparatus 27; and at the same time, the incoming gas control apparatus 24 is started for replenishing the gas. To further improve the uniformity and cleanliness of the gas inside the incubator body 16, one or more gas mixing apparatuses 25 are placed in the incubator 16 to keep the gas in the incubator body 16 in a turbulent state so as to maintain the gas uniformity. To precisely adjust the process parameters of the gas in the incubator body 16, the incubator body 16 is further provided therein with a gas control apparatus 26. The gas control apparatus 26 comprises, but is not limited to, various types of gas concentration detecting meters, heating apparatuses, humidification apparatuses, temperature/humidity detection apparatuses, etc.

Although the present invention is disclosed above with preferred embodiments, they are not intended to limit the present invention, and any person skilled in the art can make possible changes and alternations without departing from the spirit and scope of the present invention. Therefore, without departing from the content of the technical solutions of the present invention, any alternation, equivalent variation and modification made to the embodiments above based on the technical essence of the present invention shall be construed as falling within the protection scope defined by the claims of the present invention.

The invention claimed is:

1. An incubator, comprising:
an incubator body, the incubator body having a variable pressure interface;
a variable pressure apparatus, variable pressure apparatus that is connected to the incubator body via the variable pressure interface and is configured to input fluctuating gas pressure into said incubator body;
a gas replenishing system, comprising:
a pressure relief apparatus for releasing the gas in said incubator body, and
a gas supply system for supplying a gas with stable gas concentration, gas temperature, and gas humidity to the incubator body while the pressure relief apparatus releases pressure, the gas supply system comprising:
a premixing tank that receives the one or more types of gases via an input pipeline and that is connected to the incubator body via an output pipeline, wherein a gas mixing apparatus and a gas control apparatus are disposed inside of the premixing tank;
a gas source control apparatus disposed in the input pipeline, the gas source control apparatus comprising:
a heating apparatus, and
a humidification apparatus; and
an incoming gas control apparatus disposed in the output pipeline, the incoming gas control apparatus comprising:
a heating apparatus, and
a humidification apparatus,
wherein the gas control apparatus disposed inside the premixing tank comprises:
a gas concentration detecting meter,
a heating apparatus,
a humidification apparatus, and
an apparatus for detecting temperature and humidity.

2. The incubator according to claim 1, wherein said variable pressure apparatus comprises:
a cylinder body; and
a piston, wherein
the cylinder body is communicated to the incubator body via the variable pressure interface, and
the piston is movably disposed in the cylinder body so as to input the gas pressure by means of the movement of the piston.

3. The incubator according to claim 2, wherein the cylinder body is connected to the variable pressure interface directly or via a pipe.

4. The incubator according to claim 2, wherein
the cylinder body is directly connected to the variable pressure interface, and
the variable pressure interface is large enough to allow the cylinder body and the incubator body to synchronously change in gas pressure along with the movement of the piston.

5. The incubator according to claim 2, wherein
the cylinder body is fixedly connected to the incubator body, and the cylinder body is fixedly connected to the top of said incubator body.

6. The incubator according to claim 2, wherein
the variable pressure apparatus further comprises at least one of an electric cylinder, a pneumatic cylinder, or a hydraulic cylinder;
preferably, the electric cylinder comprises:
a servo motor, and
a transmission mechanism that connects the servo motor and the piston to convert the rotation of the servo motor into the movement of the piston; and
the electric cylinder is an electric push rod that drives the piston to move.

7. The incubator according to claim 1, wherein the variable pressure apparatus comprises:
a gas storage tank that is communicated to said incubator body via a pressurization gas circuit and a decompression gas circuit, wherein
the pressurization gas circuit includes a pressurization pump and a pressurization control valve, wherein
the pressurization pump is configured to transport a gas in the gas storage tank to the incubator body, and
the pressurization control valve is configured to control the on-off of the pressurization gas circuit; and
the decompression gas circuit includes a decompression pump and a decompression control valve, wherein
the decompression pump is configured to transport a gas in the incubator body to the gas storage tank, and
the decompression control valve is configured to control the on-off of the decompression gas circuit.

8. The incubator according to claim 1, wherein said incubator body further includes a safety valve that is opened after the pressure in the incubator body exceeds a safety threshold.

9. The incubator according to claim 1, wherein the incubator body further comprises:
an openable/closable gas inlet; and
an openable/closable gas outlet that is independent of the variable pressure interface.

10. The incubator according to claim 1, wherein at least one of a sterilization apparatus, another humidification apparatus, or an electric heating apparatus is disposed in the incubator body.

11. The incubator according to claim 10, wherein the sterilization apparatus is an ultraviolet light emitter or a steam sterilization apparatus.

12. The incubator according to claim 1, wherein one or more types of gases are present in the incubator.

13. The incubator according to claim 1, wherein the incubator body further comprises:
a gas mixing apparatus disposed within the incubator body, wherein
the gas mixing apparatus is configured to keep the gas in the incubator body in a turbulent state to maintain the uniformity of the gas.

14. The incubator according to claim 1, wherein at least one of the gas source control apparatus or the incoming gas control apparatus comprises a gas filter apparatus.

15. The incubator according to claim 12, wherein the incubator is a three-gas incubator.

16. The incubator according to claim 12, wherein the types of gases include at least one of carbon dioxide, nitrogen, or oxygen.

* * * * *